(12) United States Patent
Dasbach et al.

(10) Patent No.: US 9,427,527 B2
(45) Date of Patent: Aug. 30, 2016

(54) FIXED-DOSE MEDICAMENT DELIVERY DEVICE

(71) Applicant: SANOFI-AVENTIS DEUTSCHLAND GMBH, Frankfurt am Main (DE)

(72) Inventors: Uwe Dasbach, Frankfurt am Main (DE); Verena Hofmann, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 14/382,186

(22) PCT Filed: Feb. 25, 2013

(86) PCT No.: PCT/EP2013/053663
§ 371 (c)(1),
(2) Date: Aug. 29, 2014

(87) PCT Pub. No.: WO2013/127720
PCT Pub. Date: Sep. 6, 2013

(65) Prior Publication Data
US 2015/0080809 A1 Mar. 19, 2015

(30) Foreign Application Priority Data
Mar. 2, 2012 (EP) .................................. 12157968

(51) Int. Cl.
*A61M 5/32* (2006.01)
*A61M 5/315* (2006.01)
*A61M 5/20* (2006.01)

(52) U.S. Cl.
CPC ........ *A61M 5/31555* (2013.01); *A61M 5/2033* (2013.01); *A61M 5/31595* (2013.01); *A61M 5/3243* (2013.01); *A61M 5/31591* (2013.01); *A61M 2005/208* (2013.01); *A61M 2005/3267* (2013.01); *A61M 2205/581* (2013.01)

(58) Field of Classification Search
CPC ................. A61M 2005/2013; A61M 5/2033; A61M 5/326
USPC .......................... 640/198, 207–211, 192–197
See application file for complete search history.

(56) References Cited

U.S. PATENT DOCUMENTS

2011/0196339 A1* 8/2011 Hirschel ............. A61M 5/2033
604/506

FOREIGN PATENT DOCUMENTS

| WO | 2011/095486 | | 8/2011 | |
| WO | 2011/101383 | | 8/2011 | |
| WO | WO 2011101383 A1 | * | 8/2011 | .......... A61M 5/2033 |

* cited by examiner

*Primary Examiner* — Phillip Gray
(74) *Attorney, Agent, or Firm* — Fish & Richardson P.C.

(57) ABSTRACT

A medicament delivery device is presented having a housing, a safety sleeve movable between an extended position and a retracted position relative to the housing, a guide sleeve rotatably disposed in the housing, a plunger slidably disposed in the safety sleeve, and a button coupled to the housing. When the safety sleeve is in the retracted position, translation of the button relative to the housing causes the guide sleeve to rotate relative to the safety sleeve. Rotation of the guide sleeve relative to the safety sleeve allows the plunger to translate a predetermined axial distance relative to the safety sleeve.

18 Claims, 3 Drawing Sheets

FIXED-DOSE MEDICAMENT DELIVERY DEVICE

CROSS REFERENCE TO RELATED APPLICATIONS

The present application is a U.S. National Phase Application pursuant to 35 U.S.C. §371 of International Application No. PCT/EP2013/053663 filed Feb. 25, 2013, which claims priority to European Patent Application No. 12157968.4 filed Mar. 2, 2012. The entire disclosure contents of these applications are herewith incorporated by reference into the present application.

TECHNICAL FIELD

The invention relates to a fixed-dose medicament delivery device.

BACKGROUND

Administering an injection is a process which presents a number of risks and challenges for users and healthcare professionals, both mental and physical.

Injection devices typically fall into two categories—manual devices and autoinjectors. In a conventional manual device, a user must provide force to drive a medicament through a needle. This is typically done by some form of button/plunger that has to be continuously pressed during the injection. There are numerous disadvantages for the user from this approach. For example, if the user stops pressing the button/plunger, the injection will stop and may not deliver an intended dose to a patient. Further, the force required to push the button/plunger may be too high for the user (e.g., if the user is elderly). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices. Autoinjectors may be single-dose, delivering the entire contents of a cartridge or pre-filled syringe, or may be fixed-dose, delivering predetermined amounts from the cartridge or pre-filled syringe.

There remains a need for an improved, fixed-dose autoinjector.

SUMMARY

It is an object of the present invention to provide a fixed-dose medicament delivery device.

In an exemplary embodiment, a medicament delivery device according to the present invention comprises a housing, a safety sleeve movable between an extended position and a retracted position relative to the housing, a guide sleeve rotatably disposed in the housing, a plunger slidably disposed in the safety sleeve, and a button coupled to the housing. When the safety sleeve is in the retracted position, translation of the button relative to the housing causes the guide sleeve to rotate relative to the safety sleeve. Rotation of the guide sleeve relative to the safety sleeve allows the plunger to translate a predetermined axial distance relative to the safety sleeve.

In an exemplary embodiment, the medicament delivery device further comprises a cartridge of a medicament disposed in the housing. The cartridge includes a stopper slidably disposed in the cartridge.

In an exemplary embodiment, the housing is adapted to engage a needle assembly having a needle. In the extended position, the safety sleeve covers the needle.

In an exemplary embodiment, the medicament delivery device further comprises a safety sleeve spring biasing the safety sleeve toward the extended position.

In an exemplary embodiment, the medicament delivery device further comprises a plunger spring biasing the plunger relative to the housing.

In an exemplary embodiment, the plunger includes an arm adapted to engage a slot on the safety sleeve. The arm extends through the slot and engages a step element on the guide sleeve. The arm moves from a first step to a second step under the biasing force of the plunger spring when the guide sleeve rotates relative to the safety sleeve. The stopper moves the predetermined axial distance relative to the cartridge.

In an exemplary embodiment, the guide sleeve includes at least one guide pin adapted to engage one or more of a plurality of ribs on the safety sleeve when the safety sleeve is in the extended position. The one or more of the plurality of ribs disengage the at least one guide pin when the safety sleeve is in the refracted position. The button includes one or more projections adapted to engage the at least one guide pin when the button translates relative to the housing and wherein the engagement of the one or more projections and the at least one guide pin causes the guide sleeve to rotate relative to the safety sleeve.

In an exemplary embodiment, the medicament delivery device further comprises a cap removably engaging at least one of the safety sleeve and the housing.

In an exemplary embodiment, the medicament delivery device further comprises a button spring biasing the button relative to the housing.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
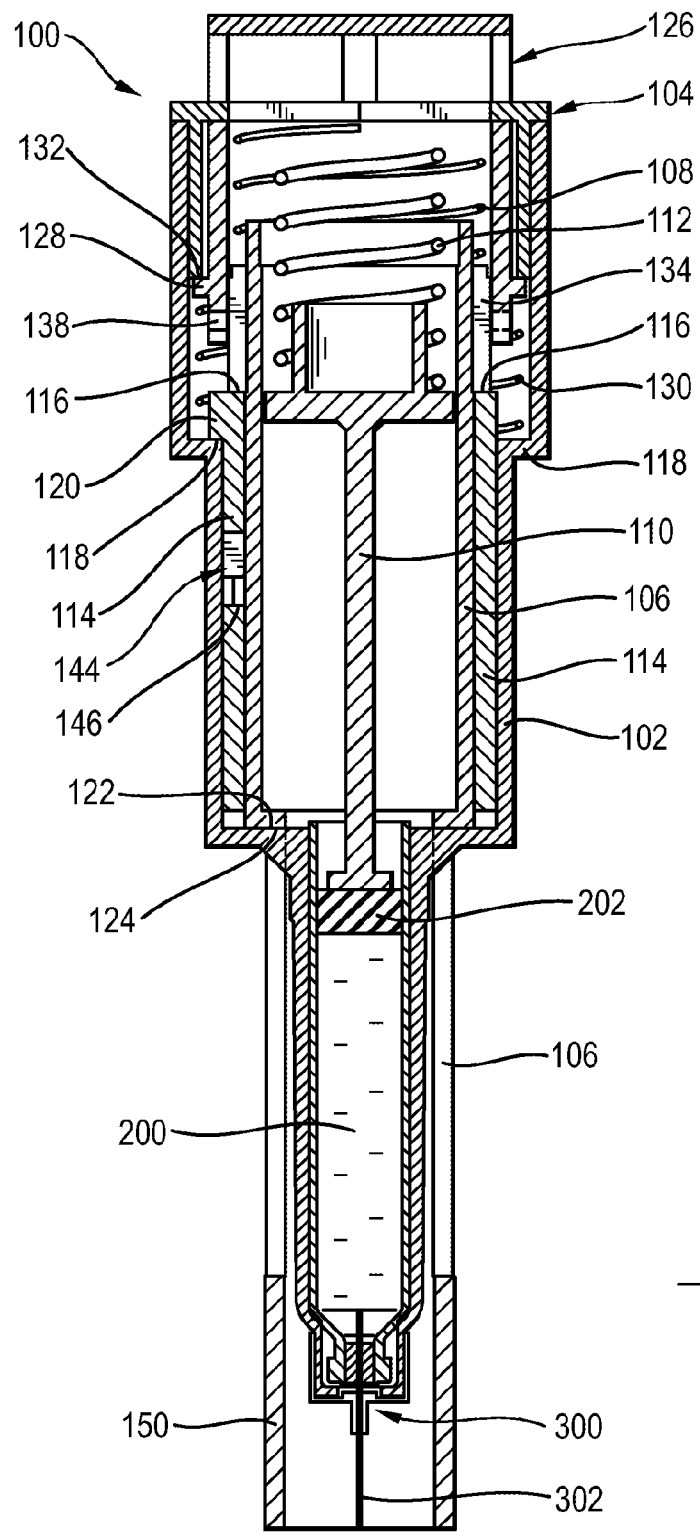
FIG. 1 shows an exemplary embodiment of a medicament delivery device according to the present invention before use.

FIG. 1 shows an exemplary embodiment of a medicament delivery device 100 according to the present invention. While the exemplary embodiment of the delivery device 100 will be described with respect to a fixed-dose delivery device, those of skill in the art will understand that the present invention may include, but is not limited to, an autoinjector, a pen injector, a syringe, a safety syringe, etc.

In an exemplary embodiment, the delivery device 100 comprises a housing 102 which is adapted to hold a cartridge 200 of a medicament. In an exemplary embodiment, the cartridge 200 is adapted to removably engage a disposable needle assembly 300, and thus, the delivery device 100 can deliver multiple doses from the cartridge 200 by replacing a used needle assembly with a new, sterile needle assembly. Those of skill in the art will understand that in other exemplary embodiments, the delivery device 100 may utilize a pre-filled syringe with an integral needle or a detachable needle (e.g., Luer Lok). The housing 102 may include a rear cap 104 which can be integrally formed with the housing 102 or attachable to the housing 102 (e.g., via snap-fit, threads, friction, welding, adhesive, etc.). After inner components of the delivery device 100 are assembly, the rear cap 104 may be coupled to the housing 102.

The cartridge 200 may be a conventional cartridge which includes a stopper 202 that is slidably disposed in the cartridge 200 and can translate relative to the cartridge 200 to dispense the medicament. If the cartridge 200 is adapted to removably engage a disposable needle assembly 300, the cartridge 200 may include a coupling mechanism (e.g., threads, a bayonet fit, a snap fit, a friction fit) that engages the needle assembly 300. In this exemplary embodiment, the cartridge 200 may include a septum at its distal end which is pierced by a proximal-facing tip of the needle assembly 300 when the needle assembly 300 is engaged to the cartridge 200.

In an exemplary embodiment, a safety sleeve 106 is telescopically coupled to the housing 102. A safety sleeve spring 108 may resiliently bias the safety sleeve 106 relative to the housing 102. In an exemplary embodiment, the safety sleeve spring 108 is grounded proximally on a surface of the rear cap 104 and proximally on a ledge on the safety sleeve 106. The safety sleeve 106 may be an elongate, cylindrical element which has an extended position and a retracted position relative to the housing 102. As shown in FIG. 1, the safety sleeve 106 is in the extended position, covering the needle assembly 300 (and, in particular, a needle 302 extending distally therefrom). In the extended position, the safety sleeve 106 prevents needlestick injuries and can alleviate fear of needles, because the needle 302 is hidden. In an exemplary embodiment, the safety sleeve 106 or a portion thereof (e.g., a distal portion covering the needle 302) can be opaque, semi-opaque, patterned, etc. In the retracted position, the safety sleeve spring 108 compresses, and the safety sleeve 106 translates in the proximal direction relative to the housing 102, exposing the needle 302.

In an exemplary embodiment, a plunger 110 is slidably disposed in the safety sleeve 106. A distal end of the plunger 110 engages the stopper 202 in the cartridge 200, and a proximal portion of the plunger 110 supports a plunger spring 112 which is proximally grounded on the rear cap 104. The plunger spring 112 may be pre-stressed such that it biases the plunger 110 in the distal direction relative to the housing 102.

In an exemplary embodiment, the safety sleeve 106 may be disposed at least partially within a guide sleeve 114. The guide sleeve 114 may be rotatable relative to the safety sleeve 106. The guide sleeve 114 may be prevented from translating relative to the safety sleeve 106 and the housing 102, because a projection 120 may abut proximal shoulders 116 on the safety sleeve 106 and abut proximal shoulders 118 on the housing 102. The biasing force of the safety sleeve spring 108 may ensure that projection 120 is retained between the proximal shoulders 116, 118.

In an exemplary embodiment, translation of the safety sleeve 106 relative to the housing 102 may be limited by distal shoulders 122 on the safety sleeve 106 abutting distal shoulders 124 on the housing 102.

In an exemplary embodiment, a button 126 is slidably disposed on a proximal portion of the housing 102. For example, the button 126 may extend through the rear cap 104 into the housing 102. A distal portion of the button 126 may include a ledge 128 which supports a button spring 130, the other end of which is grounded on the proximal shoulder 118 of the housing 102. The button spring 130 biases the button 126 in the proximal direction relative to the housing 102. Axial movement of the button 126 in the proximal direction relative to the housing 102 may be limited by a rib formed on the housing 102 or an abutment surface 132 formed on the rear cap 104.

In an exemplary embodiment, the delivery device 100 may include a removable cap (not shown) which is coupleable to the safety sleeve 106 and/or the housing 102. For example, the cap may engage the housing 102 and prevent the safety sleeve 106 from translating relative to the housing 102.

Figure 2:
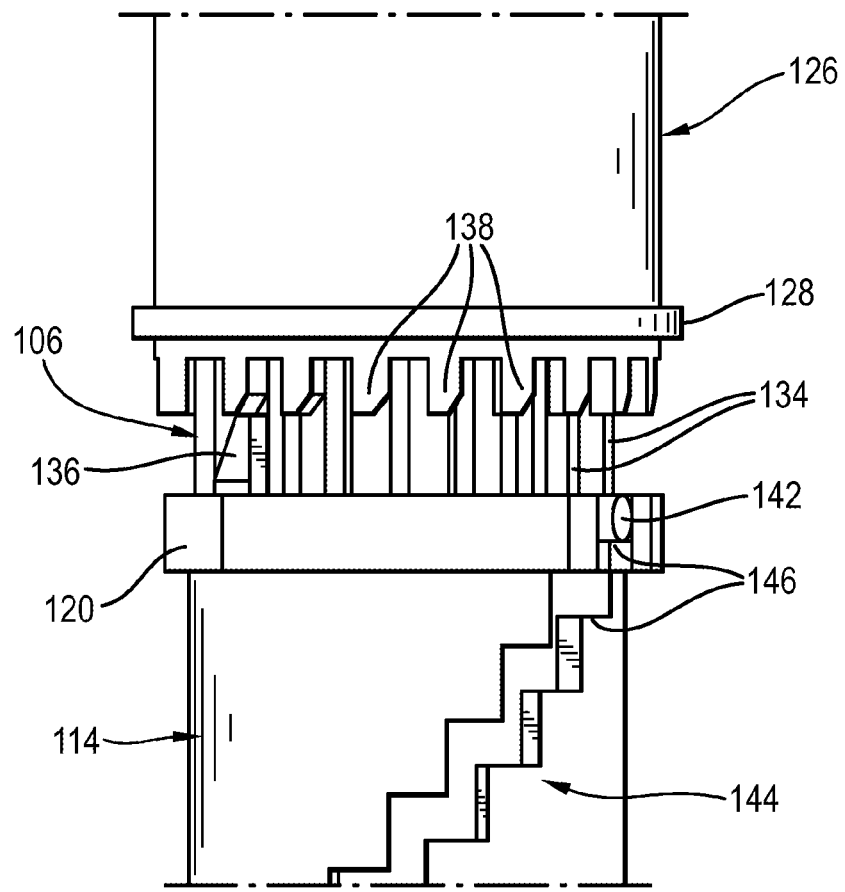
FIG. 2 shows an exemplary embodiment of a dosing mechanism of a medicament delivery device according to the present invention.
Figure 3:
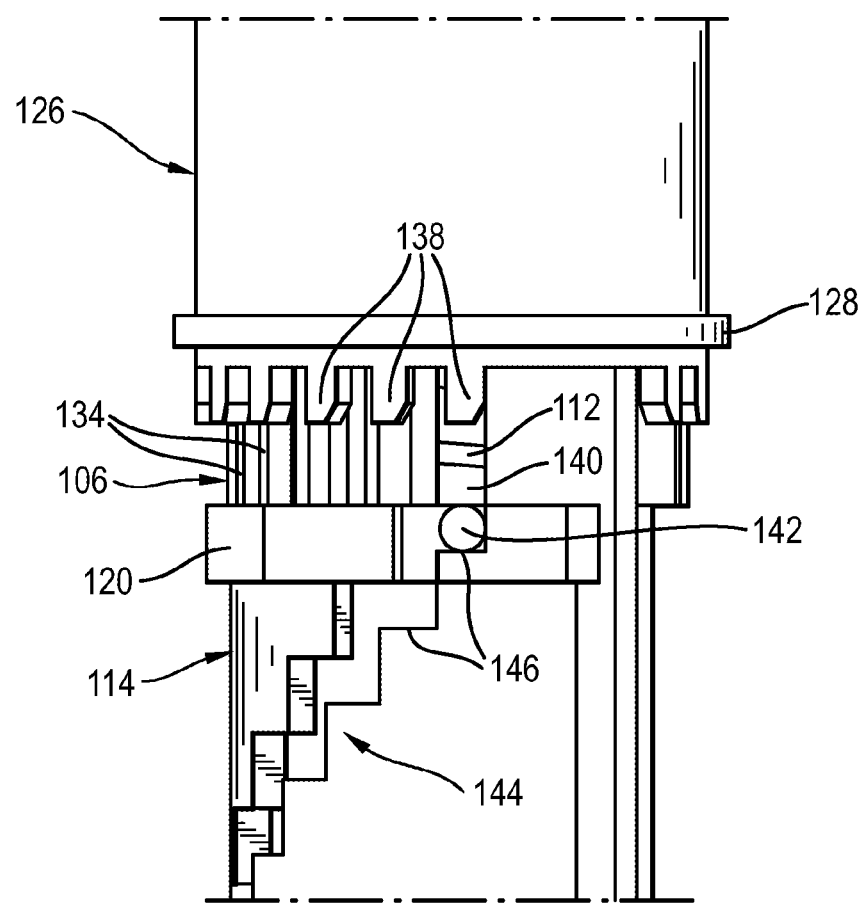
FIG. 3 shows an exemplary embodiment of a dosing mechanism of a medicament delivery device according to the present invention.

FIGS. 2 and 3 show an exemplary embodiment of a dosing mechanism according to the present invention. As shown in the exemplary embodiment in FIG. 2, at least a portion of the safety sleeve 106 may have one or more axial ribs 134 which are adapted to engage at least one guide pin 136 which projects proximally from a proximal end of the guide sleeve 114 when the safety sleeve 106 is in the extended position. In an exemplary embodiment, the number of ribs 134 is equal to or greater than the number of intended doses to be delivered by the delivery device 100. When the guide pin 136 engages the axial ribs 134, the guide sleeve 114 is prevented from rotating relative to the safety sleeve 106. When the safety sleeve 106 is in the retracted position, the guide pin 136 is not constrained by the axial ribs 134, and the guide sleeve 114 can rotate relative to the safety sleeve 106.

In an exemplary embodiment, the button 126 includes one or more projections 138 which, when the button 126 is pressed, are adapted to engage the guide pin 136 and push the guide pin 136 (and the guide sleeve 114) in a first rotational direction. In an exemplary embodiment, the number of projections 134 is equal to or greater than the number of intended doses to be delivered by the delivery device 100.

As shown in the exemplary embodiment in FIG. 3, the safety sleeve 106 includes a slot 140. A transverse arm 142 on the plunger 110 extends through the slot 140 and engages a step element 144. In an exemplary embodiment, the step element 144 comprises a plurality of steps 146 formed in at least a portion of the guide sleeve 114. The steps 146 may be formed such that adjacent steps are offset by a predetermined axial distance, which corresponds to a dose amount. As the guide sleeve 114 rotates relative to the safety sleeve 106, the arm 142 (and the plunger 110) advances, under the pressure of the plunger spring 112, to an adjacent step. As the plunger 110 moves relative to the safety sleeve 106, the dose of the medicament is delivered.

In use, a cap may be removed from the safety sleeve 106 and/or the housing 102 before an injection. In an exemplary embodiment, the cap may include a gripping portion to releaseably engage a needle assembly 300. For example, the cap may engage an unused needle assembly 300 (and/or a cover on the unused needle assembly) and be used to couple the unused needle assembly 300 to the housing 102. The delivery device 100 may be placed against an injection site. As the delivery device 100 is advanced toward the injection site, the safety sleeve 106 moves from the extended position to the retracted position and the needle 302 may be inserted into the injection site. The dosing mechanism cannot be activated (e.g., because the guide pin 136 abuts the axial ribs 134 and the guide sleeve 114 cannot rotate) until the safety sleeve 106 is in the retracted position.

When the button 126 is pressed, the projection 138 on the button engages the guide pin 136 and causes the guide pin 136 (and the guide sleeve 114) to rotate relative to the safety sleeve 114 and the housing 102. Those of skill in the art will understand that the projection 138 and the guide pin 136 may have corresponding ramped surfaces to facilitate rotation of the guide sleeve 114 and decrease the amount of force necessary to apply to the button 126 to effect the rotation.

When the guide sleeve 114 rotates, the arm 142 moves from a step 146 into an adjacent step due to the rotation of the guide sleeve 114 relative to the safety sleeve 106 and the biasing force of the plunger spring 112 acting on the plunger 110. As the plunger 110 translates axially, it advances the stopper 202 to expel a dose of the medicament from the cartridge 200 through the needle 302 into the injection site.

When the button 126 is released, the biasing force of the button spring 130 causes the button 126 to move in the proximal direction relative to the housing 102, and the projection 138 disengages the guide pin 136.

When the delivery device 100 is removed from the injection site, the biasing force of the safety sleeve spring 108 causes the safety sleeve 106 to translate distally relative to the housing 102, thereby covering the needle 302. As the safety sleeve 106 translates distally, the axial ribs 134 are aligned with the guide pin 136 to prevent rotation of the guide sleeve 114 relative to the safety sleeve 106.

In an exemplary embodiment, a feedback may be provided when an injection is complete and/or when the cartridge 200 is empty. For example, a sound (e.g., a click or a snap) may be generated when the arm 142 moves into and abuts an adjacent step. Also for example, a window (not shown) may be formed in the housing 102 over a last step in the step element 144, and the arm 142 may have an indicia (e.g., a color). When the indicia is visible through the window, the feedback may be provided that the cartridge 200 is empty.

In an exemplary embodiment, a distal end of the safety sleeve 106 may include a removable shield 150, as shown in FIG. 1. The shield 150 may be coupled to the safety sleeve 106 by, for example, threads, a bayonet coupling, a snap fit, a friction fit, a hinge, etc. The shield 150 may be removed to provide access to the distal end of the housing 102 for attaching and/or removing a needle assembly 300 from the housing 102.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39), des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medicament delivery device comprising:
a housing;
a safety sleeve movable between an extended position and a retracted position relative to the housing;
a guide sleeve rotatably disposed in the housing, the guide sleeve comprising at least one guide pin adapted to engage one or more of a plurality of ribs on the safety sleeve when the safety sleeve is in the extended position;
a plunger slidably disposed in the safety sleeve; and
a button coupled to the housing, the button comprising one or more projections adapted to engage the at least one guide pin of the guide sleeve such that the guide sleeve rotates relative to the safety sleeve upon translation of the button relative to the housing when the safety sleeve is in the retracted position,
wherein rotation of the guide sleeve relative to the safety sleeve allows the plunger to translate a predetermined axial distance relative to the safety sleeve.

2. The medicament delivery device according to claim 1, further comprising:
a cartridge of a medicament disposed in the housing, wherein the cartridge includes a stopper slidably disposed in the cartridge.

3. The medicament delivery device according to claim 1, wherein the housing is adapted to engage a needle assembly having a needle.

4. The medicament delivery device according to claim 3, wherein, in the extended position, the safety sleeve covers the needle.

5. The medicament delivery device according to claim 1, further comprising:
a safety sleeve spring biasing the safety sleeve toward the extended position.

6. The medicament delivery device according to claim 1, further comprising:
a plunger spring biasing the plunger relative to the housing.

7. The medicament delivery device according to claim 1, wherein the plunger includes an arm adapted to engage a slot on the safety sleeve.

8. The medicament delivery device according to claim 7, wherein the arm extends through the slot and engages a step element on the guide sleeve.

9. The medicament delivery device according to claim 7, wherein the arm moves from a first step to a second step under a biasing force of a plunger spring when the guide sleeve rotates relative to the safety sleeve.

10. The medicament delivery device according to claim 2, wherein the stopper moves the predetermined axial distance relative to the cartridge.

11. The medicament delivery device according to claim 1, wherein the one or more of the plurality of ribs disengage the at least one guide pin when the safety sleeve is in the retracted position.

12. The medicament delivery device according to claim 1, further comprising:
a cap removably engaging at least one of the safety sleeve and the housing.

13. The medicament delivery device according to claim 1, further comprising:
a button spring biasing the button relative to the housing.

14. The medicament delivery device according to claim 1, wherein the at least one guide pin of the guide sleeve projects proximally from a proximal end of the guide sleeve.

15. The medicament delivery device according to claim 1, wherein each of the at least one guide pin and the ribs comprises a ramped surface to facilitate rotation of the guide sleeve when the button is translated relative to the housing.

16. The medicament delivery device according to claim 1, wherein the safety sleeve is disposed at least partially within the guide sleeve.

17. The medicament delivery device according to claim 1, wherein the guide sleeve comprises a projection configured to abut a shoulder of the safety sleeve to inhibit relative translation between the guide sleeve and the safety sleeve.

18. The medicament delivery device according to claim 8, wherein the step element is a first step element, and the guide sleeve comprises a second step element offset from the first step element by the predetermined axial distance.

* * * * *